United States Patent [19]

Wright et al.

[11] 4,178,452

[45] Dec. 11, 1979

[54] ETHYL 3-[(3,4-DIMETHOXYPHENYL)E-THYLAMINO]-1,2,5,6-TETRAHYDRO-2-OXOPYRIDINE-4-CARBOXYLATE

[75] Inventors: George C. Wright; Ronald E. White, both of Norwich, N.Y.

[73] Assignee: Morton-Norwich Products, Inc., Norwich, N.Y.

[21] Appl. No.: 967,364

[22] Filed: Dec. 7, 1978

[51] Int. Cl.$^2$ .................................................. C07D 213/55
[52] U.S. Cl. ........................................ 546/297; 424/266
[58] Field of Search .......................................... 546/297

[56] References Cited

U.S. PATENT DOCUMENTS 3,951,992  4/1976  Meyer et al. .......................... 546/297

Primary Examiner—Alan L. Rotman
Attorney, Agent, or Firm—Anthony J. Franze

[57] ABSTRACT

Ethyl 3-[(3,4-dimethoxyphenyl)ethylamino]-1,2,5,6-tetrahydro-2-oxopyridine-4-carboxylate is useful as a muscle relaxant.

1 Claim, No Drawings

ETHYL 3-[(3,4-DIMETHOXYPHENYL)ETHYLAMINO]-1,2,5,6-TETRAHYDRO-2-OXOPYRIDINE-4-CARBOXYLATE

This invention relates to the chemical compound ethyl 3-[(3,4-dimethoxyphenyl)ethylamino]-1,2,5,6-tetrahydro-2-oxopyridine-4-carboxylate. It possesses pharmacologic activity. Particularly, it exhibits skeletal muscle relaxant activity when administered to warm blooded animals. Upon intravenous administration of it to rats in a dose of about 25 mg/kg, inhibition of gastrocnemius muscle twitch is elicited. Suitable vehicles for intravenous administration include physiologically acceptable menstrua such as dimethylsulfoxide, tetrahydrofuryl alcohol and dimethylacetamide.

The compound of this invention can be readily formulated into pharmaceutical compositions such as tablets, elixirs, solutions, suspensions, capsules and the like using excipients and adjuvants commonly employed for such purposes and with which there is no incompatibility.

In order that this invention may be readily available to and understood by those skilled in the art, the following method of preparing it is described:

A. Ethyl 2,3-Dioxo-4-piperidinecarboxylate

A few crystals of iodine and a small amount of $Hg_2Cl_2$ were introduced into a mixture of benzene (2 liters) and ethanol (280 ml). Sodium methoxide (108 g, 2.0 moles) was added with stirring. A mixture of 2-pyrrolidone (17.2 g, 2.0 moles) and diethyl oxalate (292 g, 2.0 moles) was introduced in large increments. Slight exothermicity was observed. The reaction mixture was refluxed for 24 hours. It was acidified with 320 ml of 1:1 HCl. The hot benzene was decanted, the salt and water were mixed with fresh boiling benzene, and the benzene was decanted. This extraction with boiling benzene was done three times. The extracts were combined and filtered by gravity. The filtrate was concentrated under reduced pressure to approximately 1.5 liters. This was concentrated on a steam bath to approximately 600 ml. On cooling overnight, a solid (151 g, m.p. 148°–151°) was obtained. Yield: 40.7%.

B. Ethyl 3-[(3,4-Dimethoxyphenyl)ethylamino]-1,2,5,6-tetrahydro-2-oxopyridine-4-carboxylate A 185.0 g portion of A (1.0 mole) in 3000 ml toluene was treated with homoveratrylamine (190.0 ml, 1.05 mole) and 0.5 ml conc. HCl, then refluxed for 3 hours until all the $H_2O$ was removed via a Dean-Stark trap. The mixture was allowed to cool to R.T. overnight, then filtered and stripped of solvent under reduced pressure. Yield: 145.0 g, (42%).

The product was recrystallized from benzene-anhydrous ether (1:2), refrigerated before collecting, and the crystals were washed with anhydrous ether, m.p. 58°–60°.

Anal. Calcd. for $C_{18}H_{24}N_2O_5$: C, 62.05; H, 6.94; N, 8.04. Found: C, 62.42; H, 6.78; N, 7.62.

What is claimed is:

1. The compound ethyl 3-[(3,4-dimethoxyphenyl)ethylamino]-1,2,5,6-tetrahydro-2-oxopyridine-4-carboxylate.